(12) United States Patent
Barnett

(10) Patent No.: US 6,428,573 B2
(45) Date of Patent: Aug. 6, 2002

(54) INTRAOCULAR MULTIFOCAL LENS CONSTRUCTION

(76) Inventor: Howard J. Barnett, 6006 Balcones Ct. #15, El Paso, TX (US) 79912

( * ) Notice: Subject to any disclaimer, the term of this patent is extended or adjusted under 35 U.S.C. 154(b) by 0 days.

(21) Appl. No.: 09/761,737

(22) Filed: Jan. 18, 2001

Related U.S. Application Data

(60) Provisional application No. 60/180,043, filed on Feb. 3, 2000.

(51) Int. Cl.$^7$ .................................................. A61F 2/16
(52) U.S. Cl. ...................................... 623/6.27; 623/6.28
(58) Field of Search ............................. 623/6.23, 6.24, 623/6.25, 6.27, 6.28; 351/161

(56) References Cited

U.S. PATENT DOCUMENTS

| 3,420,006 A | 1/1969 | Barnett |
| 3,420,976 A | 1/1969 | Morris et al. |
| 3,471,976 A | 10/1969 | Barnett |
| 4,458,454 A | 7/1984 | Barnett |
| 4,898,461 A | 2/1990 | Portney |
| 5,225,858 A | 7/1993 | Portney |
| 5,684,560 A | 11/1997 | Roffman et al. |

Primary Examiner—Dinh X. Nguyen
(74) Attorney, Agent, or Firm—Nixon & Vanderhye PC

(57) ABSTRACT

An intraocular multifocal lens has no definite line between near, far, and/or intermediate power lens areas, and substantially no distortion. A human or animal can use the lens with no need for it to translate. The lens preferably has substantially circular, substantially concentric, lens areas in order from the center, far, intermediate, and near. The multifocal zone preferably is about 2.5–3.5 mm in diameter for all adults. The lens can be made by mechanically acting on a single vision lens (having a predetermined near prescription) using a spinner shaft mounting the lens, and a rotating dish covered by a taut fabric.

24 Claims, 2 Drawing Sheets

INTRAOCULAR MULTIFOCAL LENS CONSTRUCTION

This application claims the benefit of U.S. Provisional Application No. 60/180,043, which was filed Feb. 3, 2000. The disclosure of which is incorporated herein by this reference.

BACKGROUND AND SUMMARY OF THE INVENTION

The invention relates to an intraocular multifocal lens, and methods of manufacture and utilization thereof. The need for and advantages of the invention are best understood by reviewing the background in the normal operation of the accommodative mechanism of the eye.

Using the most accepted explanation of accommodation, that of Helmholtz, it is known that as an object approaches an emmetropic or artificially emmetropic eye the rays from the object become more and more divergent. If the eye remains unchanged, the refracted rays strike the retina before coming to a focus. Thus, the object appears blurred (blurred, but not distorted). In the normal visual system this blur is the mechanism that triggers the brain to cause the ciliary muscles to contract which allows the crystalline lens to increase its plus power in order to focus the diverging rays on the retina to produce a clear image. Thus the eye accommodates itself to the nearer object so as to obtain a clear image. Objects closer or further are blurred, but not distorted, and are ignored unless they become the new object of interest.

In eyes which have lost all (as in cataract extraction, aphakia) or part of their accommodative mechanism as with presbyopia (due to increased age and usually beginning between ages 40–45) this focusing at near is either lost or reduced, the severity depending upon the condition of the eye and age of the individual. Normally, a bifocal spectacle or bifocal contact lens is prescribed so that the patient has clear vision at the far point (i.e. 20 feet and beyond) and at reading distance. By definition a bifocal has two foci, one for far vision and one for near. If the difference between these powers is significant there is an intermediate range of blurred vision between near and far.

In order for the wearer to use the different powers of the average bifocal his or her eye must look through one part of the lens for distance vision and through the other part of the lens for near vision. This requires that the patient holds his or her head up and his or her eyes down in an abnormal position in order to see at near. Since there is a line of demarcation between these two powers he or she sees a split image as his or her eye passes across this junction, and notices objects change position as the powers change suddenly (commonly termed "Bifocal Jump").

Some have attempted to eliminate or at least reduce this problem by "smearing" the junction line between the two powers, but have really only induced a new problem, distortion. Very few people can tolerate distortion of any amount as this is an abnormal condition to the human eye and brain. As stated earlier, blur is normal and can be tolerated at least until accommodation produces a clear image.

There is a differentiation among spectacle lenses, contact lenses and intraocular lenses in the details of vision mechanism.

(1) Spectacle lenses require significant head movement so that the eyes can see through the distance, intermediate (if available) and near portions of the lens.

(2) Contact lenses must be able to move. If a contact lens does not move it will become intolerable to the eye due to dryness, deposits, edema, infection, etc.

(3) An intraocular lens, implanted in the eye, normally does not move. Thus the design of the lens regarding the distance, intermediate and near lens areas must be definitely different from the spectacle and contact lens.

What is needed to properly correct aphakia is an intraocular lens which has the following characteristics:

(a) When implanted in the patient's eye he or she need only to look normally at objects he or she wishes to see at any distance and in any position.

(b) No definite line of demarcation between near and far so that no split image, distortion, glare, etc. is seen and the patient has clear vision at all distances—far, near and intermediate.

(c) The transition between far and near powers must be smooth, gradual, and without distortion. These powers must be available to the patient so that he or she can use them to see at the intermediate distances.

It can readily be seen that with a lens as described above the patient has available all of the powers he or she needs to see clearly without distortion at any distance. His or her brain need only select the power that makes any object clear. The same triggering mechanism, blur, that is used with normal accommodation is used with this lens to cause the eye and brain to select the proper power. As with normal accommodation as stated earlier the brain ignores other blurred images until they become the object of interest.

In order to satisfy the above characteristics it is necessary to produce a lens that has all of the powers the patient needs to see clearly at any distance and make them available, without distortion, in a lens which cannot translate. Thus all of the powers must be available simultaneously in a very small multifocal zone size.

According to the present invention an intraocular multifocal lens is provided with no definite line between near and far or intermediate powers, no distortion, and no need for the lens to translate, e.g. as the patient has all of the powers in a circular conformation on either the front or back of the lens or both.

Another parameter of the lens of the invention is that the very center of the lens should be the distance or far correction surrounded by the intermediate powers and finally the near or reading powers. While the lens could be made in reverse, with the near in the center surrounded by the intermediate powers and then by the distance power, this relationship does not normally perform as well and is not recommended.

The process for producing a multifocal intraocular lens differs from that used to produce multifocal contact lenses, or other lenses, in several ways:

(1) The multifocal zone size is smaller in the intraocular lens since the lens does not move, is closer to the retina than a contact lens and is very close to the iris and pupil. The zone size may be determined by evaluating the length of the eye by using an "A" scan along with the necessary power of the correcting lens and the pupil size. A longer eye might need a larger zone size as would a lens which does not center well. While a smaller pupil size might require a smaller zone size as would a shorter eye. While the multifocal zone size can be varied as discussed above it has been found by extensive research and trial and error that a uniform zone size of about 2.5–3.5 (e.g. about 3) mm in diameter for essentially all adults is appropriate.

(2) Working with intraocular lenses is considerably different than with spectacle or contact lenses. Since the eye is aphakic and the lens will be implanted in aqueous, intraocular lenses average about 17–24 diopters in aqueous and about 52–73.5 in air while contact lenses and spectacle lenses average about 1–4 diopters in air.

(3) Also, the diameter of an intraocular lens is usually about 5–6.5 mm, e.g. about 6 mm, but can vary considerably, while contact lenses are usually about 9–14 mm and spectacle lenses are considerably larger than the other two and vary greatly in size and shape.

According to one aspect of the present invention an intraocular multifocal lens is provided. The intraocular multifocal lens according to the invention has no definite line between near, far, or intermediate power lens areas, and substantially no distortion.

In the preferred construction of the multifocal lens of the invention, the lens has substantially concentric and substantially circular near, intermediate, and far power lens areas. Preferably the far power lens area is centrally located in the lens, and at least one intermediate power lens portion is between the near and far power lens areas. Preferably the multifocal zone is about 2.5–3.5 mm (e.g. about 3 mm) in diameter. While the invention in its simplest form may comprise only three different curvature areas, it is to be understood that in the preferred embodiment there are many, many (perhaps several hundred or more) slightly different powers in each of the near, intermediate, and far areas, and the terminology is to be interpreted with this in mind.

Typically the lens has a front surface adapted to be remote from a user's retina, and a rear surface adapted to be closer to a user's retina; and the near, intermediate and far power lens areas are formed in at least one of the front and rear surfaces. The near, intermediate, and far power lens areas may be formed only in the front surface, only in the rear surface, or both the front and rear surfaces. Typically the lens has a diameter of about 5–6.5 mm, e.g. about 6 mm, and a diopter of between about 52–73.5 in air. No aspheric curve which causes distortion, but rather a multiplicity of spherical powers, is provided for the lens according to the invention.

According to another aspect of the present invention there is provided (a) producing an intraocular multifocal lens having no definite line between near, far, or intermediate power lens areas, and substantially no distortion. And (b) placing the intraocular lens from (a) in a human's or animal's eye.

In the preferred method of the invention, (a) is practiced by mechanically acting on a curved surface of a single vision lens which has the power of the human's (or animal's) near eye prescription to provide lens areas thereof that have intermediate and far power for the patient. Also, (a) may be further practiced by forming the intermediate and far power lens areas so that they are substantially circular in configuration and substantially concentric. Still further, (a) may be practiced so that the intermediate power lens area is concentric with and surrounds a far power lens area that is substantially centrally located in the lens, and the near power lens area surrounds the intermediate power lens area. For example (a) is further practiced using a spinner shaft and a spinning dish having fabric tightly stretched thereover, and by (a1) releasably fixing the lens to the spinner shaft preferably with the curved surface convex and facing away from the spinner (although the back surface could be flat, concave or convex), (a2) disposing the spinner shaft at an angle to the axis of rotation of the fabric covered dish; (a3) rotating at least one of the spinner shaft and dish, and (a4) operatively bringing the curved surface of the lens into contact with the rotating fabric (by moving at least one of the lens and fabric).

Alternatively, (a) may be practiced by producing a mold having desired lens area configurations, and then filling the mold with fluid lens material, causing the fluid lens material to harden to form the lens, and then removing the lens from the mold, or by using a laser lathe.

According to another aspect of the present invention there is provided a method of producing an intraocular multifocal lens using a single vision lens having a curved surface, using a spinner shaft, and a dish having fabric tightly stretched thereof, comprising: (a1) releasably fixing the lens to the spinner shaft with the curved surface convex and facing away from the spinner, (a2) disposing the spinner shaft at an angle to the axis of rotation of the fabric covered dish; (a3) rotating at least one of the spinner shaft and dish, and (a4) operatively bringing the curved surface of the lens into contact with the rotating fabric, to form near, intermediate, and far power lens areas that are substantially circular and substantially concentric with each other. In the practice of this aspect of the invention, preferably the single vision lens has a near power prescription for a particular human or animal eye, and (a1)–(a4) are practiced to provide a central far power lens area surrounded by an intermediate power lens area, in turn surrounded by a near power lens area. Also preferably (a1)–(a4) are practiced so that the multifocal zone formed by the near, intermediate, and far power lens areas has a diameter that is about 2.5–3.5 mm. The invention also preferably comprises an intraocular multifocal lens constructed by the method described above.

It is the primary object of the present invention to provide a highly effective intraocular multifocal lens which does not have the drawbacks associated with conventional bifocals or multifocals. This and other objects of the invention will become clear from an inspection of the detailed description of the invention and from the appended claims.

DETAILED DESCRIPTION OF THE DRAWINGS

Figure 1:
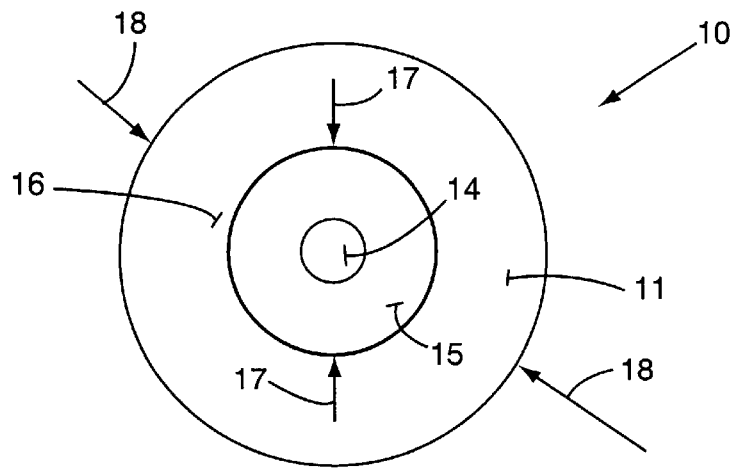
FIG. 1 is a top schematic view of an exemplary intraocular multifocal lens according to the present invention, only showing the far and intermediate lens areas shown by lines of demarcation simply for clarity of illustration.
Figure 2:
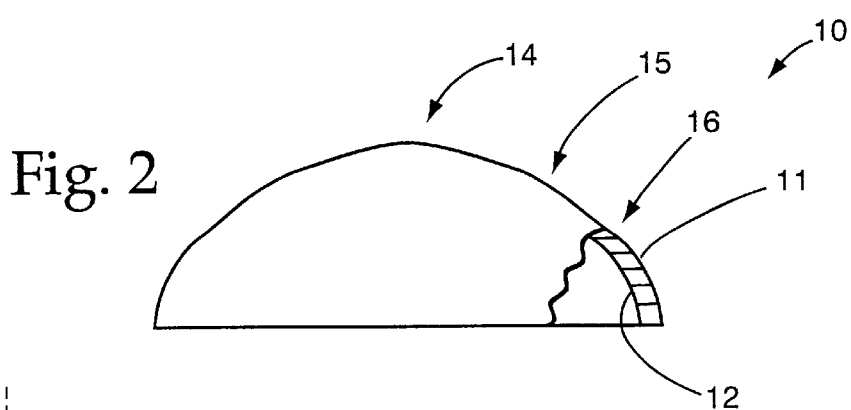
FIG. 2 is a side schematic view of the lens of FIG. 1.

An exemplary intraocular multifocal lens according to the present invention is shown generally by reference numeral 10 in FIGS. 1 and 2. The lens 10 has a convexly curved front surface 11 and a concave (as shown), flat, or even convex rear surface 12 (see FIG. 2). In FIG. 2 the degree of curvature of the lens surfaces 11, 12 is exaggerated for clarity of illustration.

The lens 10 illustrated in FIGS. 1 and 2 includes a central lens 14 which comprises a far power lens area, specifically designed for a particular human eye. Substantially concentric with and surrounding the far lens area 14 is an intermediate lens area 15 which also preferably is substantially circular in configuration, and surrounds the area 14 substantially concentric therewith. The remainder of the lens, surrounding the intermediate area 15, comprises a near power lens area. While FIG. 2 shows lines of demarcation between the lens areas 14–16, this is only for clarity of illustration, and in fact there will be no definite line between the near 16, intermediate 15, and far 14, lens areas, but rather they will have a gradual curvature or slope from one to the other as well as within areas 14 and 15. The gradual curvature or slope between the portions 14–16 is schematically illustrated in FIG. 2. Also, there will be substantially no distortion. Also it should be noted that in the preferred embodiment each of the areas 14–16 has a plurality of different powers, perhaps in the hundreds, the powers gradually moving from lowest at the true center to highest at the outermost concentric portion of the lens. Once the outside edge of the multifocal zone is reached the lens 10 may remain at full near power for the particular patient involved.

As also seen in FIG. 1, preferably the multifocal portion, that is, that portion of the lens 10 having the far and intermediate and part of the near 14, 15, 16, respectively, typically has a diameter, indicated between the arrows 17 in FIG. 1, of about 2.5–3.5 mm, e.g. about 3 mm. The typical intraocular lens 10 has an outside diameter, indicated by the arrows 18 in FIG. 1, of about 5–6.5 mm, e.g. about 6 mm. Also as an intraocular lens it typically has a diopter of about 52–73.5 in air.

While the lens 10 according to the present invention may be made in a wide variety of manners, one preferred manner is utilizing equipment such as shown in U.S. Pat. Nos. 3,420,006, 3,471,976, and 4,458,454, the disclosures of which are hereby incorporated by reference herein. Some of the elements of this equipment are illustrated schematically in FIG. 3, namely the spinner shaft 20, the dish (also referred to as a bowl) 21 with an open top that is covered by a taut fabric, such as a cotton cloth, 22, and mounted for powered rotation about a shaft 23. The fabric 22 is held stretched across the open top of the dish 21 by one or more rubber bands, a rubber O-ring, a coil spring, or a strap, all collectively schematically illustrated by the structure 23 in FIG. 3.

Figure 3:
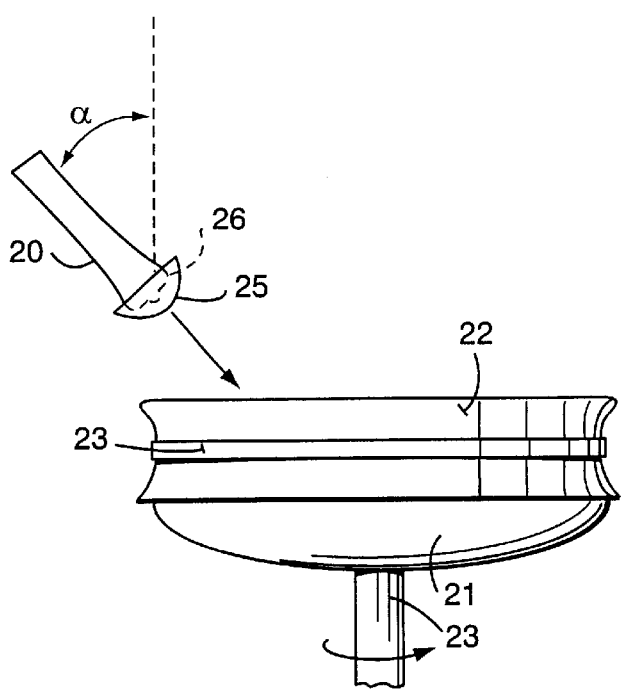
FIG. 3 is a schematic side view of exemplary equipment that may be utilized to make the intraocular lens of FIGS. 1 and 2.

To produce a lens 10 preferably one starts with a single vision lens 25 which has the power of the patient's near prescription for the eye in which the ultimate lens 10 is to be utilized. A toric lens may be used if desired in some circumstances, especially for patients with astigmatisms. The front curve of the single vision lens (as can be seen in FIG. 3) is substantially spherical, as is the base curve, so that the final multifocal lens 10 produced is essentially the same. By flattening a part of the front surface (the front curve) of the lens 25 the power of the lens would be reduced in plus power. The purpose of utilizing the equipment illustrated in FIG. 3 and described in the above referenced patents is to generate the multifocal areas, i.e. to form the various lens areas 14, 15, etc.

The single spherical power (or toric) lens 25 is mounted to the spinner shaft 20 and held thereto by double sided tape, pitch, dental wax, or like material, shown schematically and in dotted line at 26 in FIG. 3. The spinner shaft 20 is held at an angle to the spinning dish 21 and the fabric 22 is coated with a suitable polishing compound. As described in the aforementioned patents, the dish 21 can be of varying diameters and depths which changes the relationship of the different areas 14, 15, etc. of the power of the lens 10 that is ultimately procured. The angle a will vary depending upon how large the multifocal zone (between arrows 17) is; if a larger zone size is desired a greater angle α is used, while a smaller angle α is used to create a smaller zone. The lens 25 also can be held at varying distances from the center of the spinning fabric 22. A greater distance increases the speed with which the lens 25 spins on the spinner shaft 20.

Although preferably the spinner shaft 20 is free spinning, it can also have a varying amount of drag to speed or slow the process, and can be power driven in either direction at various speeds instead of being free spinning. The spinner shaft 20 may be held, fixed, or part of a swivel device which moves up and down with the turn of a wheel or leveler as with a drill press. The swivel device (not shown), when utilized, allows the spinner shaft 20 to be positioned at any angle. The swivel device may be an ordinary ball and socket type swivel, or one which swivels fore and aft and side to side.

The apparatus illustrated in FIG. 3 can also be used to form and polish lens edges and peripheral curves. The base curve can be polished or changed in radius by using a convex tool of the desired radius covered by a material 22, and otherwise acted upon if the back surface is piano or concave.

While the lens 10 is preferably manufactured pursuant to the method as described with respect to FIG. 3 it is possible to produce the lens 10 by using a lathe, and/or by molding. For example, the variable curves for any given lens can be determined by generating a specific lens on a hard or dehydrated soft lens or other type lenses by using the equipment as described with respect to FIG. 3, and then reproducing those curves on a lathe or mold. For example, by using a special lathe, such as a laser lathe, the curves can be determined optically or electronically.

Figure 4:
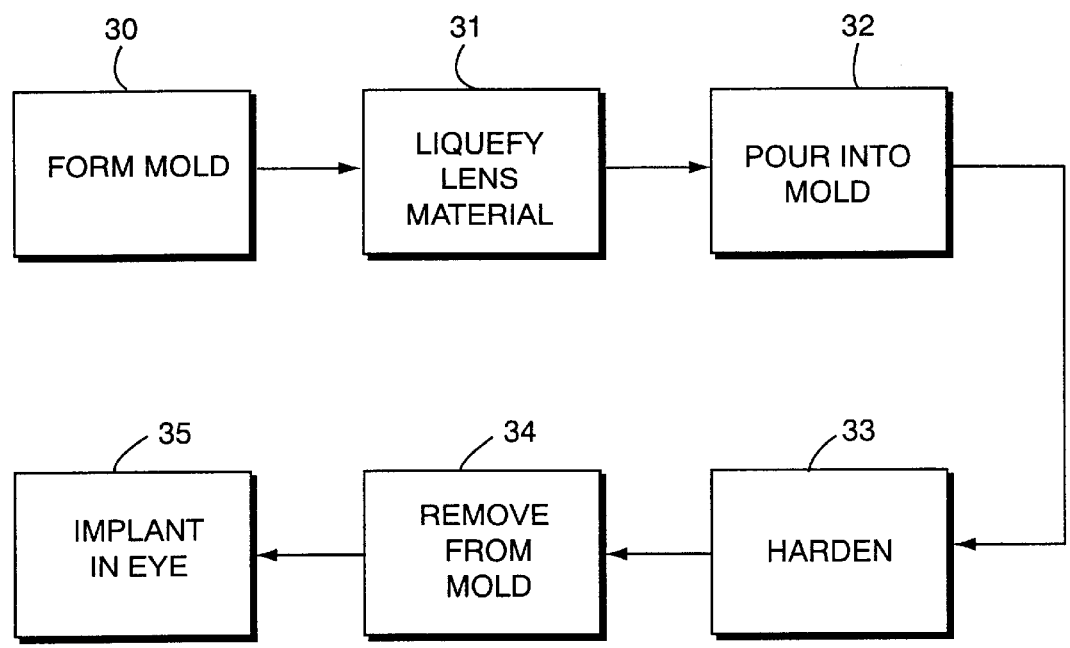
FIG. 4 is a block diagram showing another possible process for making an intraocular lens according to the invention.

FIG. 4 schematically illustrates production of a lens 10 utilizing a molding process. As illustrated by box 30, first the mold is formed, such as described above by using the equipment of FIG. 3 with a hard or dehydrated soft lens or the like. After the mold is formed, the material (plastic) or the like which is to be used to make the intraocular lens 10 is made fluid using any conventional means, as illustrated at 31, and then the fluid material is poured or otherwise placed into the mold, as schematically illustrated by box 32. Then the material is caused to harden (either at room temperature, or by blowing cool air past the mold, or in other conventional manners) as indicated by box 33. Then the lens 10 produced is removed from the mold, as illustrated schematically by box 34 in FIG. 4, and then implanted in a human or animal eye, as illustrated schematically by box 35, utilizing any conventional technique.

Utilization of lenses 10 according to the invention, produced with the equipment described with respect to FIG. 3, has been successful in all of the surgeries in which it has been employed. Three patients had multifocal lenses 10 implanted bilaterally, one patient had a lens 10 implanted in only one eye (acuity equals 20/25 & J-1) with a cataract in the other eye, and one patient had a lens 10 implanted in one eye but during the surgery of the second eye the capsule ruptured so that an anterior chamber single vision lens (no multifocal anterior chamber lens was available at the time) had to be implanted. The patient with a multifocal in one eye and a single vision in the other is actually unaware that she does not have bilateral multifocal lenses since far, near, and intermediate vision is extremely good (i.e. 20/20 & J-1) and comfortable. This is, of course, the same situation that a patient with one normal accommodating eye and only a single vision implant in the other would experience.

Three patients have bilateral multifocal implants and all see 20/20 or 20/25 in the distance and J-1 or J-2 at near OD, OS, OU with the exception of one patient who has had on amblyopic eye since childhood and therefore this eye has reduced VA far and near (20/80 & J-7) while the other eye sees 20/25 & J-1.

All binocular multifocal patients have fusion with single binocular vision as demonstrated by the Stereo Fly test, no diplopia and the positive experiences of the patients in everyday life with these lenses. Also all patients have very good vision even in reduced illumination. The small reduction in acuity in dim illumination is approximately the same as with normal phakic eyes. This is important in light of the fact that there is no known other true multifocal that does not severely reduce visual acuity in dim illumination. This was one of the reasons for their failure.

If a patient with a multifocal lens sees clearly at distance, but poorly at near or vice-versa, it is obvious that the multifocal is not performing properly. Thus, if a patient with a properly functioning multifocal implant needs a spectacle lens to see clearly in the distance, as is common in single vision implants when the surgeon selects the incorrect distance power and/or there is corneal astigmatism, then this same single vision spectacle lens will also make the patient's intermediate and near acuity clearer as with the herein described lens. If, however, the multifocal implant is not performing properly, the patient will need a different power lens at near than at far, or even worse no spectacle lens will improve acuity far and/or near. This is another way that the lens of the invention has been proven to function so well.

It will thus be seen that according to the present invention a posterior chamber or anterior chamber intraocular multifocal lens, a method of lens utilization, and a method of producing an intraocular multifocal lens from a single vision lens, and the intraocular multifocal lens produced by the method, have been provided that are highly advantageous and overcome the limitations of the prior art. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent products and methods.

What is claimed is:

1. An intraocular multifocal lens, said intraocular multifocal lens having a far power lens area, a near power lens area and an intermediate power lens area, said intermediate power lens area being defined between said near and far power lens areas, and a power transition between said far power area and said near power area being gradual so that said intraocular multifocal lens has no definite line between said near, far, or intermediate power lens areas, and substantially no distortion.

2. An intraocular multifocal lens as recited in claim 1 wherein said lens has substantially concentric and substantially circular near, intermediate, and far lens areas.

3. An intraocular multifocal lens as recited in claim 2 wherein said far power lens area is centrally located in said lens.

4. An intraocular multifocal lens as recited in claim 3 wherein said lens has a multifocal zone that is about 2.5–3.5 mm in diameter.

5. An intraocular multifocal lens as recited in claim 3 wherein said lens has a front surface adapted to be remote from a user's retina, and a rear surface adapted to be closer a user's retina; and wherein said near, intermediate and far power lens areas are formed in at least one of said front and rear surfaces.

6. An intraocular multifocal lens as recited in claim 5 wherein said near, intermediate, and far power lens areas are formed only in said front surface, or said rear surface, or both.

7. An intraocular multifocal lens as recited in claim 1 wherein each lens area has a plurality of different powers.

8. An intraocular multifocal lens as recited in claim 2 wherein each lens area has a plurality of different powers.

9. An intraocular multifocal lens as recited in claim 8 wherein said lens has a diameter of about 5–6.5 mm and a diopter of between about 52–73.5 in air.

10. A method of lens utilization comprising:
   (a) producing an intraocular multifocal lens, said intraocular multifocal lens having a far power lens area, a near power lens area and an intermediate power lens area, said intermediate power lens area being defined between said near and far power lens areas, and a power transition between said far power area and said near power area being gradual so that said intraocular multifocal lens has no definite line between said near, far, or intermediate power lens areas, and substantially no distortion; and
   (b) placing the intraocular lens from (a) in a human's or animal's eye.

11. A method as recited in claim 10 wherein (a) is practiced by mechanically acting on a curved surface of a single vision lens which has the power of the human's or animal's near eye prescription to provide lens areas thereof that have intermediate and far powers for the human or animal.

12. A method as recited in claim 11 wherein (a) is further practiced by forming the at least one intermediate power lens area, and the far power lens area, so that they are substantially circular in configuration and substantially concentric, and each area has a plurality of different powers.

13. A method as recited in claim 12 wherein (a) is further practiced so that the intermediate power lens area is concentric with and surrounds a far power lens area that is substantially centrally located in the lens, and the near power lens area surrounds the intermediate power lens area.

14. A method as recited in claim 13 wherein (a) is further practiced using a spinner shaft and a spinning dish having fabric tightly stretched thereover, and by (a1) releasably fixing the lens to the spinner shaft with the curved surface convex and facing away from the spinner, (a2) disposing the spinner shaft at an angle to the axis of rotation of the fabric covered dish; (a3) rotating at least one of the spinner shaft and dish, and (a4) operatively bringing the curved surface of the lens into contact with the fabric.

15. A method as recited in claim 10 wherein (a) is practiced by using a single vision lens having a curved surface and mechanically acting on the curved surface to provide lens areas having different powers.

16. A method as recited in claim 15 wherein (a) is further practiced using a spinner shaft and a spinning dish having fabric tightly stretched thereover, and by (a1) releasably fixing the lens to the spinner shaft with the curved surface convex and facing away from the spinner, (a2) disposing the spinner shaft at an angle to the axis of rotation of the fabric covered dish; (a3) rotating at least one of the spinner shaft and dish, and (d4) operatively bringing the curved surface of the lens into contact with the fabric.

17. A method as recited in claim 15 wherein (a) is further practiced so that the intermediate power lens area is concentric with and surrounds a far power lens area that is substantially centrally located in the lens, and the near power lens area surrounds the intermediate power lens area.

18. A method as recited in claim 10 wherein (a) is practiced by producing a mold having desired lens area configurations, and then filling the mold with fluid lens material, causing the fluid lens material to harden to form the lens, and then removing the lens from the mold.

19. A method as recited in claim 10 wherein (a) is practiced by mechanically acting on a toric lens.

20. A method as recited in claim 10 wherein (a) is practiced using a laser lathe.

21. A method of producing an intraocular multifocal lens using a single vision or toric lens having a curved surface, a spinner shaft, and a dish having fabric tightly stretched thereof, comprising:

(a1) releasably fixing the single vision spherical or toric lens to the spinner shaft with the curved surface convex and facing away from the spinner, (a2) disposing the spinner shaft at an angle to the axis of rotation of the fabric covered dish; (a3) rotating at least one of the spinner shaft and dish, and (a4) operatively bringing the curved surface of the lens into contact with the fabric, to form near, intermediate, and far power lens areas that are substantially circular and substantially concentric with each other, said intermediate power lens area being defined between said near and far power lens areas, and a power transition between said far power area and said near power area being gradual so that said intraocular multifocal lens has no definite line between said near, far, or intermediate power lens areas, and substantially no distortion.

22. A method as recited in claim 21 wherein the lens is a single vision lens that has a near power prescription for a particular human or animal eye, and wherein (a1)–(a4) are practiced to provide a central far power lens area surrounded by an intermediate power lens area, in turn surrounded by a near power lens area, each area having a plurality of different powers.

23. A method as recited in claim 22 wherein (a1)–(a4) are practiced so that the multifocal zone formed by the intermediate, near, and far power lens areas has a diameter that is about 2.5–3.5 mm.

24. An intraocular multifocal lens produced by the method of claim 23.

* * * * *